United States Patent

Larke et al.

[11] 4,109,648
[45] Aug. 29, 1978

[54] ELECTRODE ASSEMBLIES

[75] Inventors: John Reginald Larke, Birmingham; Colin Barber, Underwood; David John Cotterill, Birmingham, all of England

[73] Assignee: National Research Development Corporation, London, England

[21] Appl. No.: 750,853

[22] Filed: Dec. 15, 1976

[30] Foreign Application Priority Data

Dec. 18, 1975 [GB] United Kingdom ............... 51855/75

[51] Int. Cl.² .................................................. A61B 5/04
[52] U.S. Cl. ......................... 128/2.06 E; 128/2.1 E; 128/417; 128/DIG. 4
[58] Field of Search .............. 128/2.06 E, 2.1 E, 2 E, 128/404, 410, 411, 417, 418, DIG. 4

[56] References Cited

U.S. PATENT DOCUMENTS

| 2,525,381 | 10/1950 | Tower | 128/410 X |
|---|---|---|---|
| 2,555,037 | 5/1951 | Jensen | 128/417 |
| 2,887,112 | 5/1959 | Smith | 128/417 |
| 3,387,608 | 6/1968 | Figar | 128/2.06 E |
| 3,528,408 | 9/1970 | Opperman | 128/2.1 E |
| 3,547,105 | 12/1970 | Paine | 128/2.06 E |
| 3,580,240 | 9/1971 | Cosentino | 128/2.06 E |
| 3,893,444 | 7/1975 | Fatt | 128/2 E |
| 3,946,730 | 3/1976 | Monter | 128/2.06 E |
| 3,976,055 | 8/1976 | Monter et al. | 128/2.06 E |
| 3,989,050 | 11/1976 | Buchalter | 128/417 X |
| 3,998,215 | 12/1976 | Anderson et al. | 128/2.06 E |
| 4,008,721 | 2/1977 | Burton | 128/418 |
| 4,016,869 | 4/1977 | Reichenberger | 128/2.1 E |

FOREIGN PATENT DOCUMENTS

| 122,258 | 2/1972 | Denmark | 128/2.06 E |
|---|---|---|---|
| 1,219,017 | 1/1971 | United Kingdom | 128/419 P |

*Primary Examiner*—Robert W. Michell
*Assistant Examiner*—Lee S. Cohen
*Attorney, Agent, or Firm*—Finnegan, Henderson, Farabow & Garrett

[57] ABSTRACT

A skin electrode assembly comprises a body of hydrophylic gel, and an electrochemically inert member rendered conductive by the inclusion of carbon therein, the gel body and member being directly electrically connected. The member is suitably wholly of carbon such as graphite, and the gel body can be self-supporting or located in a dished plastics housing through which the member passes. The housing can be a fitting lens for opthalmic measurements.

11 Claims, 8 Drawing Figures

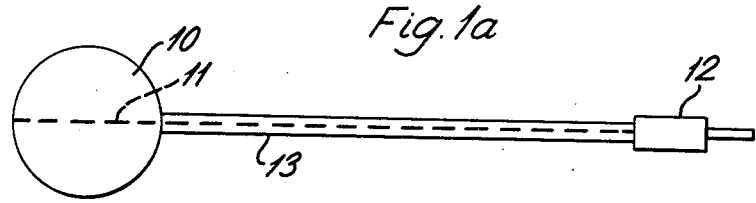
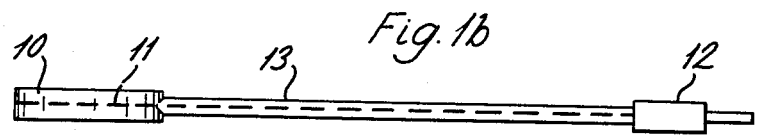
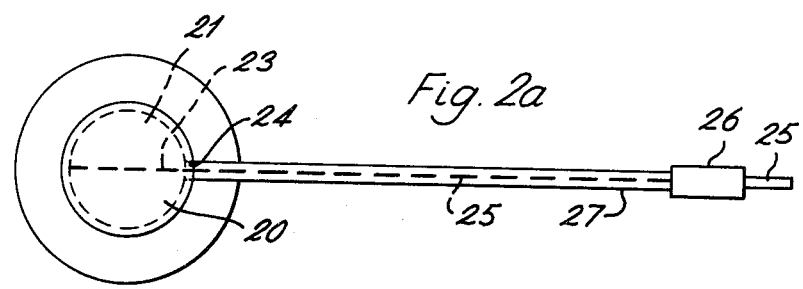
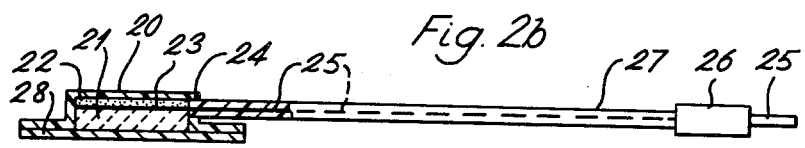

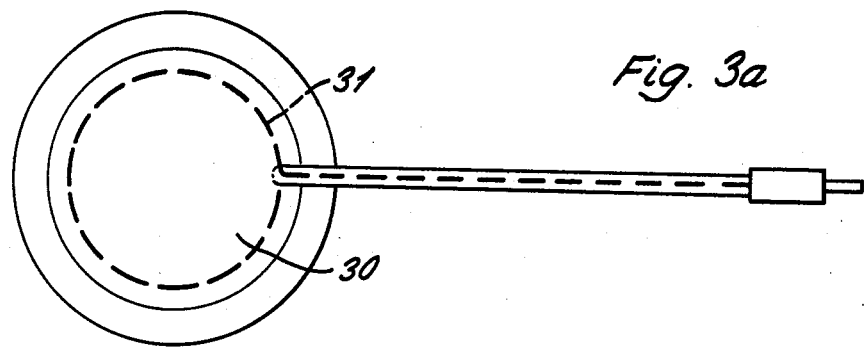
Fig. 3a
Fig. 3b
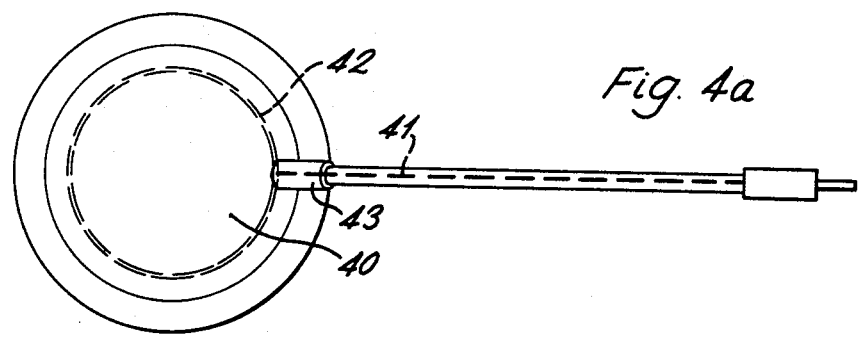
Fig. 4a
Fig. 4b

ELECTRODE ASSEMBLIES

This invention relates to electrode assemblies, and more particularly such assemblies for use in the detection of electrophysiological signals for purposes of monitoring, measurement and recording. These assemblies are often referred to as "skin electrodes" since they are usually applied to the skin of a patient.

Currently available electrode assemblies of this kind typically comprise a cupped casing of plastics material in which an electrode of noble metal is mounted with a wire lead extending from the electrode through the casing wall. In use of such an assembly, it is normal to employ an electrolyte-bearing paste or gel to provide a low resistance contact between th electrode and the skin of the patient to whom the electrode is applied.

These assemblies suffer from a variety of difficulties which largely arise from two causes. A first cause is that there is a tendency for metal ions from the electrode to enter into electrolytic solution at the electrode-electrolyte interface and to produce a potential at the electrode which can be many times larger than the signal which is to be detected. Moreover this interfering potential is sensitive to a number of different parameters. A second cause of difficulty involves the gel or paste since those in common use are invariably messy and are, on occasion, found to produce irritation and lesions of the skin to the extent that patient comfort only allows use of an electrode assembly for a limited period. This last difficulty is particularly significant if a monitoring function is to be served over an extended period.

Numerous attempts have been made to reduce individual difficulties associated with these conventional assemblies, but there appears to have been little success in any attempt to reduce substantially all of the difficulties. In contrast the present invention seeks to achieve the latter objective by avoiding the basic causes of the difficulties, namely, by avoiding the use of materials which are inherently problematical and, in particular, avoiding the use of a polarisable electrode.

To this end the present invention provides in one aspect thereof an electrode assembly for application to the skin to detect electrophysiological signals, which assembly comprises a body of electrolytic synthetic polymer of the kind called hydrophylic gels and referred to as hydrogels, and an electrochemically inert member rendered conductive by the inclusion of carbon therein, said hydrogel body and said member being directly electrically connected to each other.

In another aspect the invention provides an assembly as just defined but in which the hydrogel body is of a non-electrolytic or dehydrated form capable of being rendered electrolytic or rehydrated prior to use of the assembly.

The hydrogel body may be supported by some additional structure such as a cupped casing of plastics material, but this is not essential because more suitable hydrogels can be mechanically self-supporting to an adequate degree. The production of the hydrogel body can involve cutting from a larger pre-formed mass, pressure moulding, polymerisation in situ relative to a support, or any other suitable procedure. In practice suitable hydrogels will usually have a water content in the range 20-90% by weight. The hydrogels which have been used in the development of the invention were themselves first developed for use as soft contact lenses and descriptions of the same can be found, for example, in British Pat. Nos. 1,395,501 and 1,436,705.

The conductive member is preferably of such a form that a major part, or substantially the whole of its intrinsic content is carbon. In development of the invention use has been made of graphite cord, such as made by Le Carbone, for this purpose. Alternative materials of this form can be made from carbon fibres by braiding, spinning or felting, or by carbonising a synthetic polymer cord. However, other members may be suitable, such as an intrinsically non-conductive carrier member impregnated or otherwise loaded with carbon to render the same conductive while electrochemically inert. In any event, the conductive member can be connected to the hydrogel body by embedding, tying, or any other method which provides a satisfactory electrical connection.

Normally, it will be appropriate for the conductive member to be connected at its other end to a metal terminal serving as part of a plug, socket, or other connector for connection with associated equipment. Also, it is preferred that the conductive member be externally insulated between the hydrogel body and terminal. Such insulation is suitably effected by silicone rubber or other encapsulation allowing flexibility while adding to the mechanical strength of the member.

Electrodes according to the invention are suitable for application to skin in connection with the electro-cardiogram (ECG), electrooculogram (EOG), electrogastrogram (EGG), surface electromyogram (EMG), electrodermal response (EDR), electroencephalogram (EEG), visual evoked potential (VEP), and auditory evoked response (AER). Moreover, since hydrogels are noted for their biological inertness, being both mechanically and chemically non-irritative, assemblies according to the invention are suited to the detection of signals requiring application to sensitive areas of the exterior body surface, such as the cornea in the electroretinogram (ERG), or in body cavities where the materials of conventional assemblies may prove unsatisfactory, such as in the summated electrocochleogram (ECOG) for which the most satisfactory results are obtained adjacent the typmpanic membrane, in the detection of the electro-olfactorogram (EOGs) and the electrovaginal potentials.

The proposed assembly can be attached to the patient in different ways to suit the recording site and relevant application. For example, mechanical fixation such as with medical adhesive tape has shown good results for attachment to glabrous skin, while contact with hairy skin such as that on the scalp may require the use of the firmer fixation of collodion glue or a restraint mechanism attached to the head. Contact with the cornea of conjuctiva can be maintained by surface tension forces alone, some form of blepherostat, hard contact lens restraint, suction, or by pressure from a mechanism attached to the head or in which the head is resting.

For further clarification of the invention, it is useful to describe the detailed construction of four examples of assemblies according to the invention, these example being respectively schematically illustrated in the accompanying drawings, in which:

FIGS. 1a and 1b are respective plan and side views of a first embodiment of an electrode assembly according to the present invention;

FIGS. 2a and 2b are respective plan and longitudinal cross-sectional views of a second embodiment of the present invention;

FIGS. 3a and 3b are respective plan and longitudinal cross-sectional views of a third embodiment of the present invention; and FIGS. 4a and 4b are respective plan and longitudinal cross-sectional views of a fourth embodiment of the present invention.

The two examples of FIGS. 1 and 2 are suitable for use in ECG, EOG, EGG, EMG, EDR, EEG, VEP and AER.

In the production of the first of these examples, 1.8 gm hydroxyethyl methacrylate is polymerised with 0.012% ammonium persulphate and 0.124% sodium metabisulphite initiator in 4.2 gm water around one end of a 4 inch length of graphite fibre for one hour, to produce a 70% water content hydrogel. The resultant hydrogel is cut to produce a circular disc 10 of approximately 15 mm diameter and 1 mm thickness with the end of the graphite fibre 11 embedded therein in a diametrical location. The free end of the fibre is glued to a metal plug connector 12 using carbon-loaded conductive glue, and the remaining length of the fibre is coated with silicone rubber 13. The hydrogel disc is allowed to equilibrate in 0.9% saline (physiological) and the assembly is ready for application to the skin with polyethylene non-porous synethetic adhesive tape. The resultant assembly has an impedance of approximately 300 Ω at 1000 Hz, and satisfactory results have been obtained in each of the above uses.

The second example comprises a housing 20 of plastics material with a circular depression, of 10 mm diameter and 1 mm depth, into which is glued a complementary disc of high density graphite 21 (Le Carbone 7332). Between the glue 22 and the graphite is sandwiched the end 10 mm of a 160 mm length of a graphite fibre 23 (Le Carbone CCM 65) which extends through a hole 24 in the housing to form a lead from the electrode. The free end of the graphite fibre is trapped between the metal pin of a monopolar plus connector 25 and its plastic casing 26. The remaining exposed graphite fibre is coated with silicone rubber 27. A disc 28 of 30 mm diameter and 0.5 mm thickness, is cut from a sheet of polyhydroxyethylmethacrylate equilibrated in 0.9% saline, and placed between the skin and the high density graphite/plastic housing complex to complete the electrode assembly, which is then fixed against the skin with adhesive tape.

The two examples of FIGS. 3 and 4 have been developed for the recording of the gross ERG.

The first of these examples comprises a fitting lens 30 for ophthalmic measurement (FLOM) pressed from a sheet of methyl methacrylate. A 0.5 mm wide rectangular groove is cut from the limbal border of the back surface of the lens, a 0.5 mm diameter hole is drilled through the lens at one point in the groove, and a loop of a carbon fibre 31 is passed there-through and located in the groove to produce a ring electrode at the limbus. The inner surface of the lens is then coated with hydroxyethyl methacrylate in an equal proportion solution of ethylene glycol and distilled water in the proportions of 6:4 (hydroxyethyl methacrylate: solution) using 0.012% ammonium persulphate and 0.024% sodium metabisulphite initiator. The lens is spun at 300 rpm, in at atmosphere of nitrogen at 45° C for 90 mins, to produce an even coating 32 on the inner surface of the lens. The dehydrated hydrogel, once polymerised on the inner surface of the methyl methacrylate lens, is finished by cutting and polishing to the required curve. The remaining graphite fibre is fitted with a connector and coated as in example 1.

The remaining example again comprises a fitting lens 40 for ophthalmic measurement (FLOM) into the back surface of which a rectangular groove 0.5 mm deep is cut, a 0.5 mm hole drilled at one point, and the end of a 160 mm length of graphite fibre 41 (Le Carbone CCM 65) passed therethrough. The graphite fibre is glued into the groove so as to make mechanical and electrical contact with a high denmsity graphite ring 42 (Le Carbone 7332) which is fitted into the groove and is glued therein. The back surface of the lens is recut and polished to render the methyl methacrylate and high density graphite surfaces flush and smooth. A methyl methacrylate tube 43, of 15 mm length and 0.5 mm inside diameter is fitted and glued to the lens so as to protect the emerging graphite fibre. The remaining fibre is fitted with a plug and coated with silicone rubber as in the other examples. A soft contact lens 44 of hydrogel is located within the corneal portion of the back surface of the lens and the completed assembly is ready for use.

We claim:

1. An electrode assembly for application to the skin to detect electrophysiological signals, comprising a self-supporting body of hydrogel material, and an electrochemically inert elongate member having carbon therein to render it conductive, said member projecting from said body with one end portion thereof embedded in and connected to said body.

2. As assembly according to claim 1 wherein said member includes a core made of carbon, the other end of said member being free, an electrical terminal connected to said core at its free end, said core being coated with a flexible insulating material over its length between said body and said terminal.

3. An assembly according to claim 1 wherein said self supporting body is wholly constituted by said hydrogel material.

4. An assembly according to claim 1 wherein said body is dehydrated and capable of rehydration.

5. An electrode assembly for application to the skin to detect electrophysiological signals, comprising a dished housing of insulating plastic material; a disc formed of a first conductive material mounted in said housing and having carbon therein; an elongate member of a second conductive material projecting from said housing with one end portion of said member passing through said housing and sandwiched between said housing and said disc to electrically connect said member and said disc; the other end of said member being free said second conductive material having carbon therein; an electrical terminal connected to the free end of said member; a coating of flexible insulating material over the length of said member between said housing and said terminal; and a layer of self-supporting hydrogel material mounted on said disc to project outwardly from said housing; said first and second conductive materials being electrochemically inert and rendered conductive only by the inclusion of the carbon therein.

6. An assembly according to claim 5 wherein said member and said disc are each substantially wholly made of carbon.

7. An assembly according to claim 5 wherein said layer is dehydrated and capable of rehydration.

8. An electrode assembly for application to an eye to detect electrophysiological signals comprising: a dished housing of transparent plastic material shaped as a fitting lens for opthalmic measurement; a lenticular layer of self-supporting hydrogel material disposed over the dished surface of said housing; an elongate member having electrically conductive carbon material therein, said member projecting from said dished surface with one end portion of said member passing through said housing and extending around the peripheral portion of said dished surface in engagement with said hydrogel layer, the other end of said member being free, said conductive member being electrochemically inert and rendered conductive only by inclusion of said carbon therein; an electrical terminal connected to the free end of said member; and a coating of flexible insulating material over said member between said housing and said terminal.

9. An assembly according to claim 8 wherein said dished surface is grooved, said one end of said member being received in the groove.

10. An assembly according to claim 8 wherein said member is substantially wholly formed of carbon.

11. An assembly according to claim 8 wherein said layer is dehydrated and capable of rehydration.

* * * * *